United States Patent
Kidwell

(10) Patent No.: US 11,209,429 B2
(45) Date of Patent: Dec. 28, 2021

(54) CATALYTIC SIGNAL ENHANCEMENT FOR LATERAL FLOW IMMUNOASSAYS

(71) Applicant: The Government of the United States of America, as represented by the Secretary of the Navy, Arlington, VA (US)

(72) Inventor: David A. Kidwell, Alexandria, VA (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 38 days.

(21) Appl. No.: 16/401,411

(22) Filed: May 2, 2019

(65) Prior Publication Data

US 2019/0391138 A1    Dec. 26, 2019

Related U.S. Application Data

(60) Provisional application No. 62/666,649, filed on May 3, 2018.

(51) Int. Cl.
  *G01N 33/553*  (2006.01)
  *G01N 33/543*  (2006.01)
  (Continued)

(52) U.S. Cl.
  CPC ....... *G01N 33/54393* (2013.01); *G01N 21/78* (2013.01); *G01N 33/531* (2013.01);
  (Continued)

(58) Field of Classification Search
  CPC ........... G01N 33/558; G01N 33/54393; G01N 33/5306; G01N 33/533; G01N 33/54346;
  (Continued)

(56) References Cited

U.S. PATENT DOCUMENTS 5,384,265 A * 1/1995 Kidwell ............... G01N 33/553
                                                            435/7.5
5,637,508 A    6/1997 Kidwell et al.
(Continued)

FOREIGN PATENT DOCUMENTS

WO    WO1990006372    6/1990

OTHER PUBLICATIONS

Conyers et al., "Chromogenic Substrates fro Horseradish Peroxidase," Analytical Biochemistry, 1991, 207-211, 192.
(Continued)

*Primary Examiner* — Christopher L Chin
(74) *Attorney, Agent, or Firm* — US Naval Research Laboratory; Rebecca L. Forman

(57) ABSTRACT

The present invention provides a method for increasing the sensitivity of LFIAs by using palladium nanoparticles, selecting appropriate dye chemistries, and improving the timing of the development chemistry. In the presence of a palladium nanoparticle, three reagents interact with a catalytic label to form a colored dye. The three reagents include a hydrogen peroxide source, a color developer (a substituted para-phenylenediamine), and a color coupler (e.g. a napthol or a phenol). The timing of the development chemistry is improved by any combination of using a reducing agent, delaying hydrogen peroxide application by diffusion, using dissolving materials as a time delay, using serpentine flow, and separating the color coupler and the color developer on the strip.

5 Claims, 8 Drawing Sheets

(51) Int. Cl.
*G01N 33/531* (2006.01)
*G01N 33/58* (2006.01)
*G01N 21/78* (2006.01)
*G01N 33/53* (2006.01)
*G01N 33/533* (2006.01)
*G01N 33/558* (2006.01)
*G01N 21/77* (2006.01)
*B82Y 99/00* (2011.01)

(52) U.S. Cl.
CPC ....... *G01N 33/533* (2013.01); *G01N 33/5306* (2013.01); *G01N 33/54346* (2013.01); *G01N 33/558* (2013.01); *G01N 33/583* (2013.01); *G01N 33/587* (2013.01); *B82Y 99/00* (2013.01); *G01N 2021/7756* (2013.01)

(58) Field of Classification Search
CPC .... G01N 33/531; G01N 33/583; G01N 21/78; G01N 33/587; G01N 2021/7756; B82Y 99/00
USPC ............ 436/37, 84, 164, 172, 514, 525, 805
See application file for complete search history.

(56) References Cited

U.S. PATENT DOCUMENTS

2017/0336398 A1* 11/2017 Lin ...................... G01N 33/553
2019/0339265 A1 11/2019 Kidwell et al.

OTHER PUBLICATIONS

Fu et al., "Enhanced Sensitivity of Lateral Flow Tests Using a Two-Dimensional Paper Network Format," Anal. Chem., 2011, 7941-7946, 83.

Tominaga, "Enhanced sensitivity of lateral-flow test strip immunoassays using colloidal palladium nanoparticles and horseradish peroxidase," LWT—Food Science and Technology, 2017, 566-570, 86.

Van Dyke et al., "Luminol- or Lucigenin-Coated Micropolystyrene Beads, a Single Reagent to Study Opsonin-Independent Phagocytosis by Cellular Chemiluminescence: Reaction with Human Neutrophils, Monocytes, and Differentiated HL60 Cells," Microchemical Journal, 1990, 196-209, 41.

Tominaga, "Rapid detection of Klebsiella pneumoniae, Klebsiella oxytoca, Raoultella ornithinolytica and other related bacteria in food by lateral-flow test strip immunoassays," Journal of Microbiological Methods, 2018, 43-49, 147.

* cited by examiner

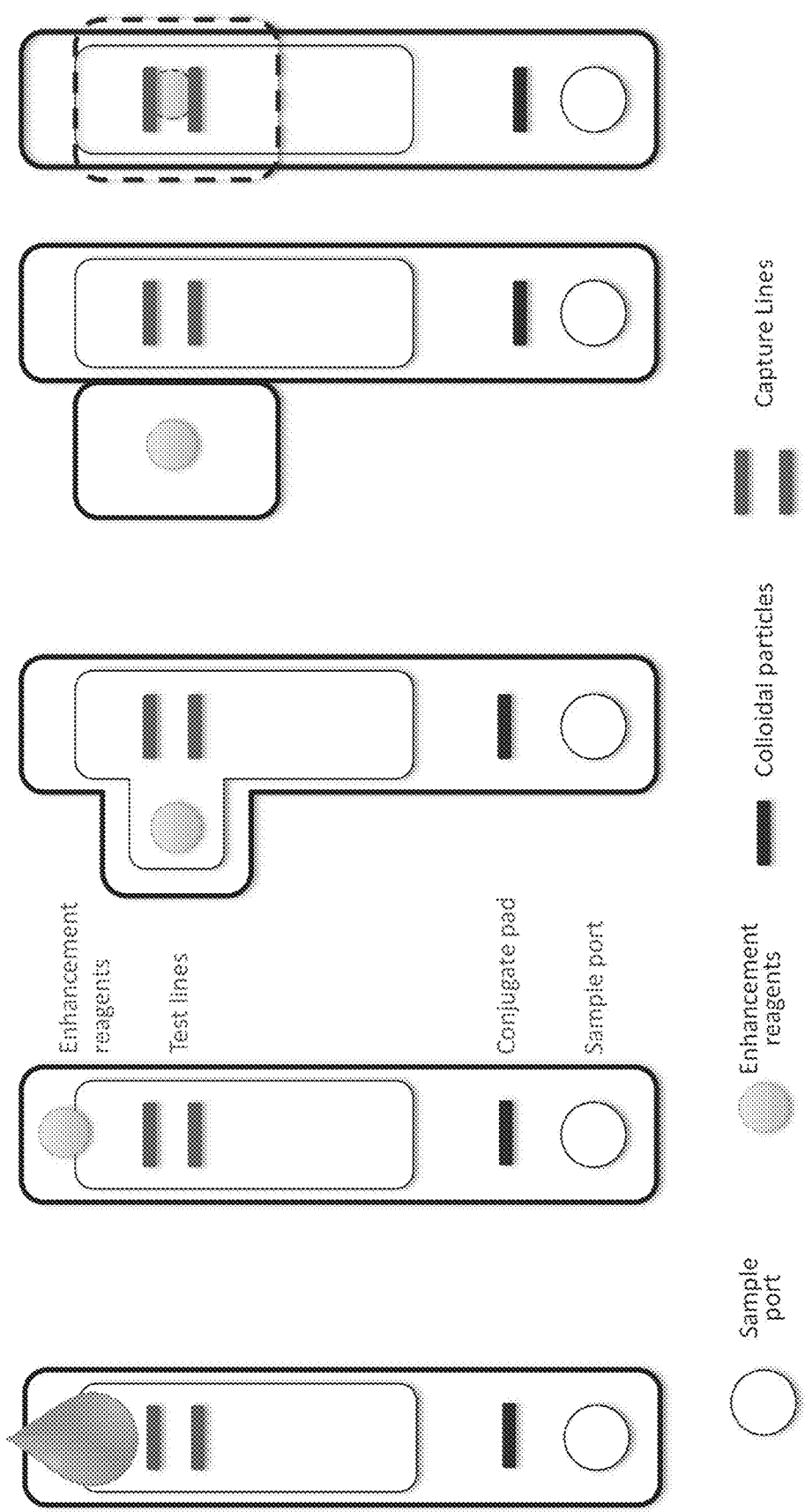

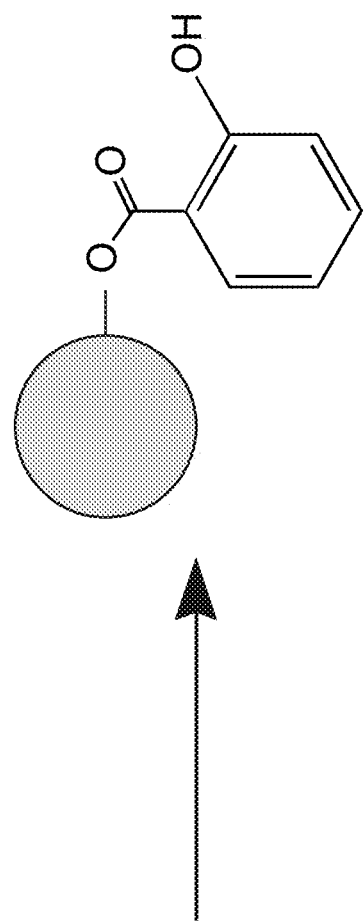
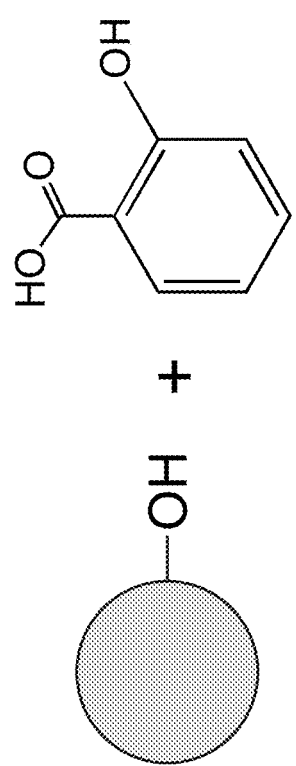
FIG. 6

CATALYTIC SIGNAL ENHANCEMENT FOR LATERAL FLOW IMMUNOASSAYS

PRIORITY CLAIM

The present application is a non-provisional application claiming the benefit of U.S. Provisional Application No. 62/666,649, filed on May 3, 2018 by David A. Kidwell, the entire contents of which is incorporated herein by reference.

Cross reference is made to application Ser. No. 16/401,418, filed contemporaneously herewith, entitled CATALYTIC PARTICLES FOR SIGNAL ENHANCEMENT FOR LATERAL FLOW IMMUNOASSAYS, by David A. Kidwell et al., the entire contents of which is incorporated herein by reference.

The present application is related to pending U.S. patent application Ser. No. 15/455,045, filed on Mar. 9, 2017 by David A. Kidwell.

BACKGROUND OF THE INVENTION

Field of the Invention

The present invention relates to enhancing catalytic signals in lateral flow immunoassays.

Description of the Prior Art

Lateral flow immunoassays (LFIAs) are widely used as point-of-care devices for surveillance and diagnostics. LFIAs can detect antigens, antibodies, peptides, proteins, toxins, and genomic sequences. They are frequently used as quick tests for diseases or conditions (e.g., home pregnancy tests, home ovulation tests, home saliva HIV tests, roadside sobriety tests for drugs of abuse, tests for diseases such as malaria and dengue). LFIAs typically use visual labels for detection. For use in in many situations, the immunoassays are typically read by the unaided eye. The general form of a LFIA is illustrated in FIG. 1, which shows a sandwich-type LFIA and demonstrates the steps in a LFIA process.

Most visually-read systems are based on either colloidal gold or colored particle labels as the visual readout. However, the color density (and hence the sensitivity) of such a system is limited to the absorbance of the particle. Although there exists a wide variety of instrumental approaches to increase the sensitivity and improve the quantitation (i.e. enzymes, fluorescence, metals, or phosphor up-converters as labels) little can be done to enhance this sensitivity if constrained to non-aided, visual readouts. For many applications, the sensitivity of LFIAs is their biggest weakness. Enzymes are an exception to the strictly absorbance-based particles as they can amplify a given binding event by enzymatically producing a colored product, but they degrade during long-term storage because they are temperature and desiccation sensitive. Alternative, non-enzymatic, catalytic, amplification systems are based on silver precipitation around the gold particles, similar to photography. This is a complex process that requires several solutions and has background issues where waiting too long will lose the signal similar to overdeveloping a photograph.

An increase in sensitivity would greatly broaden applications of LFIAs. Roadside sobriety for THC (marijuana) needs 1 ng/mL saliva, whereas the current commercial product using colloidal gold has a limit of detection of 5 ng/mL. Malaria requires <1 parasite/µL, whereas the current standard using colloidal gold is about 100 parasites/µL. The hCG required for FirstResponse® Pregnancy Test is about 10 mIU providing a 6 day window before an expected period, but increasing the sensitivity to 1 mIU would give a 14 day window before an expected period.

Typically, gold or latex reagents are used in LFIAs. An enhanced signal over conventional gold or latex reagents can be obtained by using palladium nanoparticles instead. Examples of palladium nanoparticle preparations and their use is described in U.S. patent application Ser. No. 15/455,045, filed on Mar. 9, 2017 by David A. Kidwell (referred to herein as Kidwell 2017), the entire contents of which is incorporated herein by reference.

For the LFIA in Kidwell 2017, the strip was developed using a multiple step process. This requires more user intervention than is desired. What is preferred is a single step LFIA that is user friendly with no separate solution to package for the user to apply.

BRIEF SUMMARY OF THE INVENTION

The aforementioned problems are overcome in the present invention which provides a method for increasing the sensitivity of LFIAs by using palladium nanoparticles, selecting appropriate dye chemistries, and improving the timing of the development chemistry. Three reagents interact with a catalytic label to form a colored dye. The three reagents include a hydrogen peroxide source, a color developer (a substituted para-phenylenediamine), and a color coupler (e.g. a napthol or a phenol).

The present invention has several key advantages and new features. It provides a method to use palladium nanoparticles in a rapid, catalytic preparation of a highly-colored dye at room temperature. The nanoparticles bind to proteins non-specifically—just mix and use. The results are read by the unaided eye. Sensitivity is increased 10-1000× compared to a colloidal gold assay. The results can be retained in popular formats such as two lines or +/−. Palladium nanoparticles are stable for more than a year and are dryable. The nanoparticles are heat stable to at least 80° C. (in solution) and 60+° C. on surfaces (which is more stable than typical biomolecules). Ethylenediaminetetraacetic acid (EDTA) can be incorporated to remove non-specific reactivity from other potential catalytic ions as EDTA does not affect the activity of the nanoparticles.

These and other features and advantages of the invention, as well as the invention itself, will become better understood by reference to the following detailed description, appended claims, and accompanying drawings.

BRIEF DESCRIPTION OF THE DRAWINGS

FIGS. 2A-2D show less preferred examples of incorporating reagents in a dry form to the LFIA to allow development. FIG. 2A shows where the reagents were added after the LFIA was run to develop the strip. In FIG. 2B, the reagents contact the capture lines though back diffusion. In FIG. 2C, the reagents are to the side or underneath the lines and diffusion sideways or though the strip is used to deliver the reagents. In FIG. 2D, the reagents are contained in a side strip that requires the user to place this strip onto the lines after a period of time.

FIG. 3A shows that the reagents can be separated into two groups. In FIG. 3B test solution is applied to the upper sample port and followed with another solution on the lower sample port after a period of time. In FIG. 3C, the enhancement reagents are encapsulated in a dissolvable material that takes time to dissolve. In FIG. 3D, the test reagents are to the side of the application window and diffusion timing occurs to allow them to follow the catalytic particles to the capture lines.

FIG. 6 shows immobilization of a color coupler on a particle. The particles are sufficiently large that they do not move in the flowing stream. This type of immobilization is referred to in the art as "boulders in the stream" and used on some LFIAs that have a woven surface (such as Whatman Fusion 5) rather than conventional nitrocellulose to immobilize the capture chemistry. This woven chemistry can increase flow rates and decrease non-specific binding. Suitable particles are colloidal latex, cellulose beads or glass beads, with the cellulose beads being porous having a higher surface area to volume ratio. Although the particles envisioned above may also have the capture chemistry present, to facilitate manufacturing with a single spray application, that is not required to implement the present invention. The example is shown with salicylic acid coupling as an ester to a hydroxy terminated particle but a large number of napthols or phenols or amines may be used.

DETAILED DESCRIPTION OF THE INVENTION

The present invention provides catalytic enhancement for LFIAs by focusing on development chemistry, selection of dye chemistries, and use of palladium nanoparticles.
Development Chemistry Development chemistry requires three components or reagents to interact with the catalytic label: a color coupler (e.g. a napthol (blue) or a phenol (brown or red)), a color developer—a substituted para-phenylenediamine, and a hydrogen peroxide source. To avoid development on the strip in places other than the capture lines, all reagents must be present after the biological binding event has occurred and the strip is cleared of unbound catalyst or the chemistry must be time delayed.

There are several ways to delay the development chemistry: use a reducing agent (e.g. vitamin C), add reagents later, delay hydrogen peroxide application by diffusion (e.g. placing the hydrogen peroxide source on a paper behind the strip), use dissolving materials as a time delay (e.g. sucrose/ polyethylene glycol (PEG) on strip end or in middle to slow fluid flow), use serpentine flow, separate the color coupler and the color developer on the strip (e.g. color developer in application pad and coupler near capture lines), use papers with varying wicking rates.

The regents may be impregnated into the strip along the strip or in selected locations. A limitation on incorporating all the reagents into the strip is that the development of the color will occur during the flow of the nanoparticles and cause a large background. Thus, it is necessary to separate at least one of the three required enhancement reagents from the flowing liquid.

Some examples of less preferred technology for separating at least one of the reagents from the flowing liquid are shown in FIGS. 2A-2D. FIG. 2A shows the methodology used in Kidwell 2017 where the reagents were added after the LFIA was run to develop the strip. In FIG. 2B, the reagents are in a dry form after the flow and near the absorption pad. They contact the capture lines though back diffusion. Because the diffusion of the reagents needs to cover a larger distance for the two lines, both regions will not receive the reagents at the same time and this could make quantitation difficult as one line will have a longer time and higher concentrations of the reagents. In FIG. 2C, the reagents are to the side or underneath the lines and diffusion sideways or though the strip is used to deliver the reagents to the various lines. This embodiment reduces the problems of unequal diffusion postulated in the embodiment shown in FIG. 2B. However, a connecting side strip or one under the nitrocellulose flow system can partially disturb the liquid flow and reduce the linearity of the flow front. In FIG. 2D, the reagents are contained in a side strip that requires the user to place this strip onto the lines after a period of time. This embodiment reduces the flow issues shown in FIG. 2C at the cost of increased user intervention.

Figure 1:
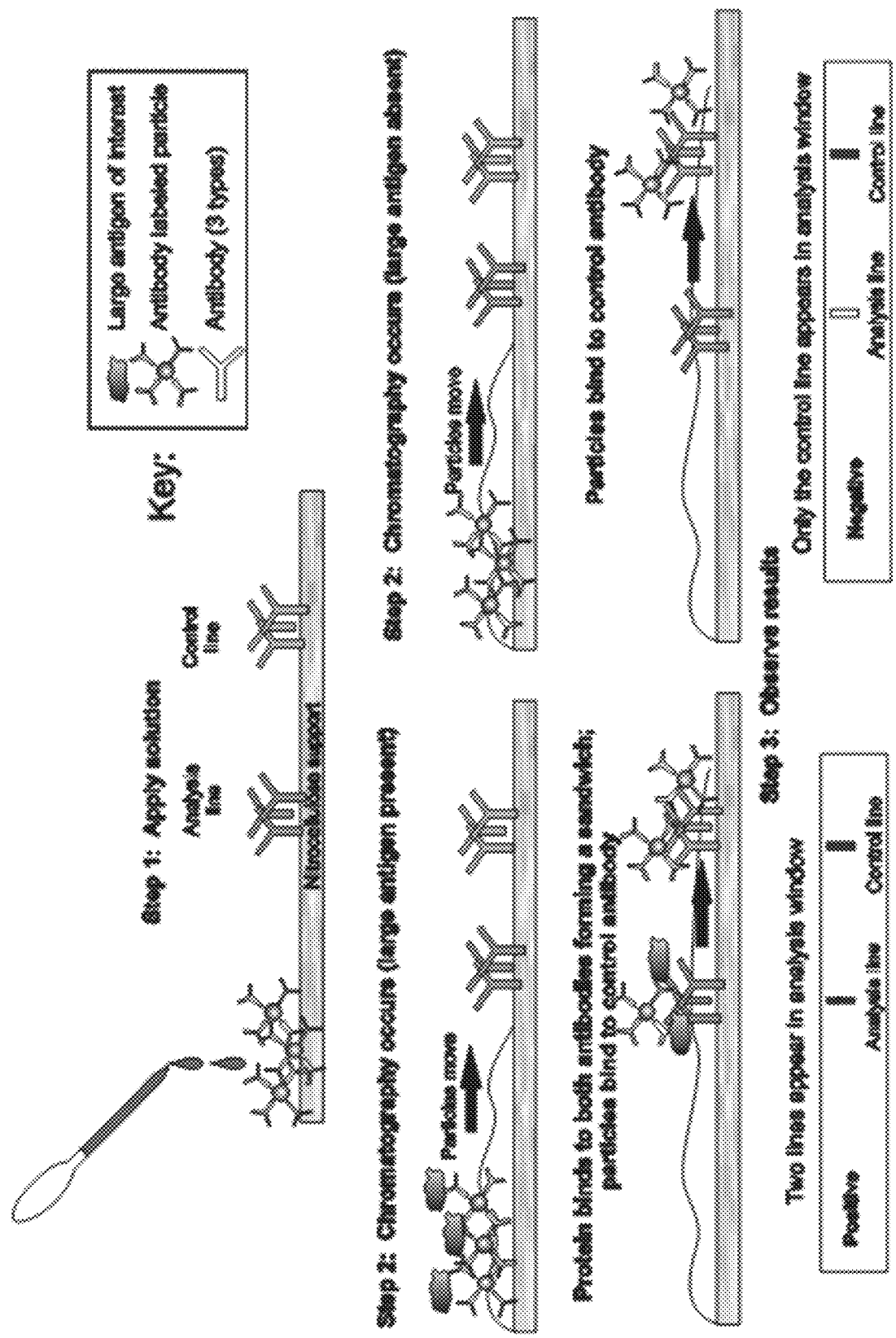
FIG. 1 is a diagram showing a sandwich-type LFIA to demonstrate the steps in a LFIA process.
Figures 3A, 3B, 3C, 3D:
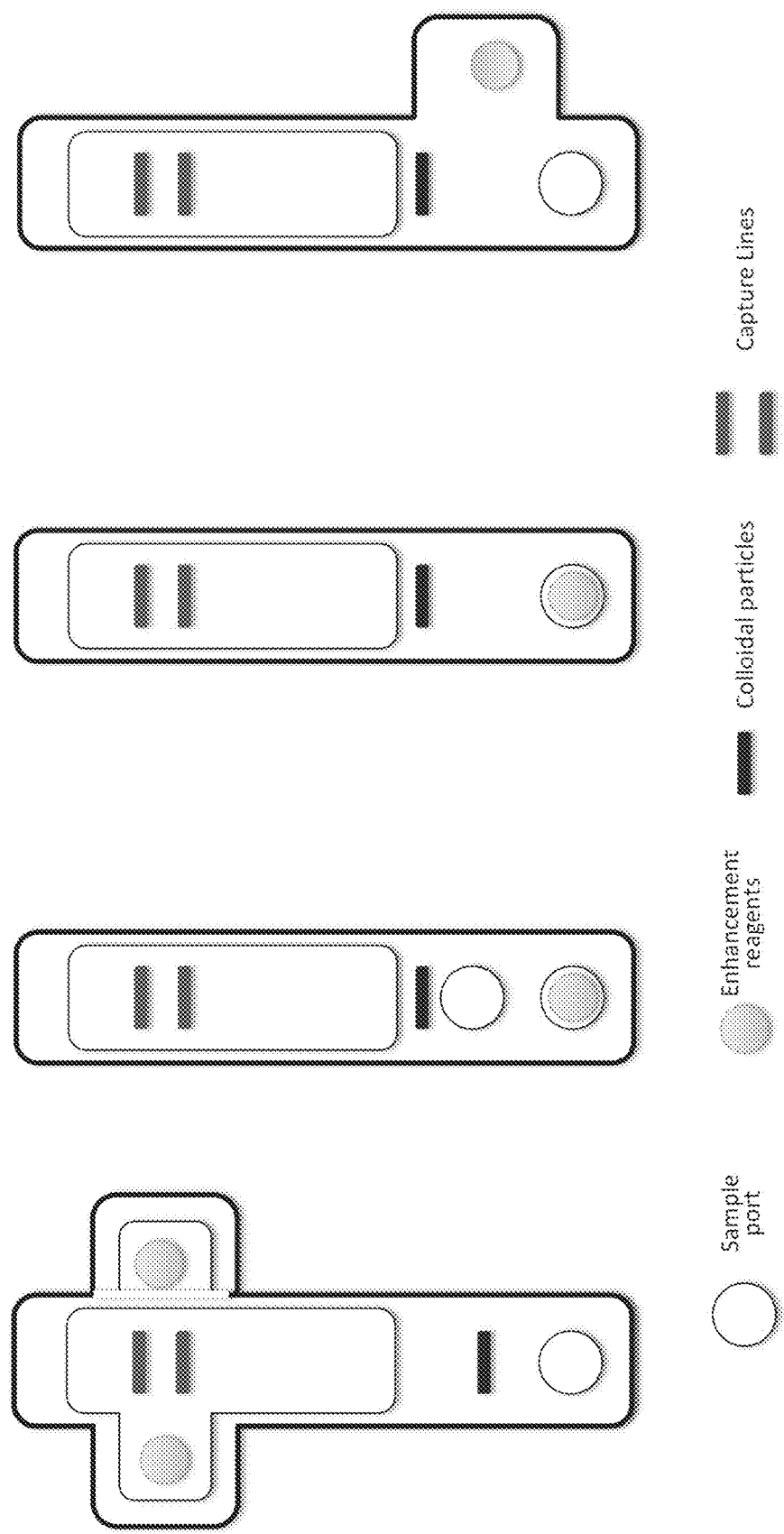
FIGS. 3A-3D show more preferred examples of incorporating reagents in a dry form to the LFIA to allow development with a minimal amount of user interaction.

Some examples of more preferred technology for separating at least one of the reagents from the flowing liquid are shown in FIGS. 3A-3D. The embodiment shown in FIG. 3A is similar to that in FIG. 2C except it overcomes some of the unequal flow limitations. It also has the advantages that the reagents can be separated into two groups. For example, the colorimetric reagents such as 4-CN and DEPDA can be dried on the left and the hydrogen peroxide precursor dried on the right. Separating the reagents increases the stability of the finished LFIA and enhances the manufacturability as the reagent pads as they can be prepared in large amounts and tested separately. The reagent pads may be any material compatible with LFIA operation, with cellulose being preferred. The embodiment shown in FIG. 3B requires that the user apply the test solution to the upper sample port and then follow with another solution on the lower sample port after a period of time. Both solutions may be the same. The second solution dissolves the reagents (which may be collocated or in different areas) and allows them to flow after the immunochromatography has occurred to develop the dye at the two capture lines. In FIG. 3C, the enhancement reagents are encapsulated in a dissolvable material that takes time to dissolve. In this case, the excess test solution from the users allows the reagent to follow the catalytic particles to the capture lines. Only a single application by the user of the test solution is necessary and the timing is all determined by the test layout. In FIG. 3D, the test reagents are to the side of the application window and diffusion timing occurs to allow them to follow the catalytic particles to the capture lines. This embodiment may be in the form of a cross as in shown in FIG. 3A to allow more uniform flow and better separation of the various reagents.

Figure 8:
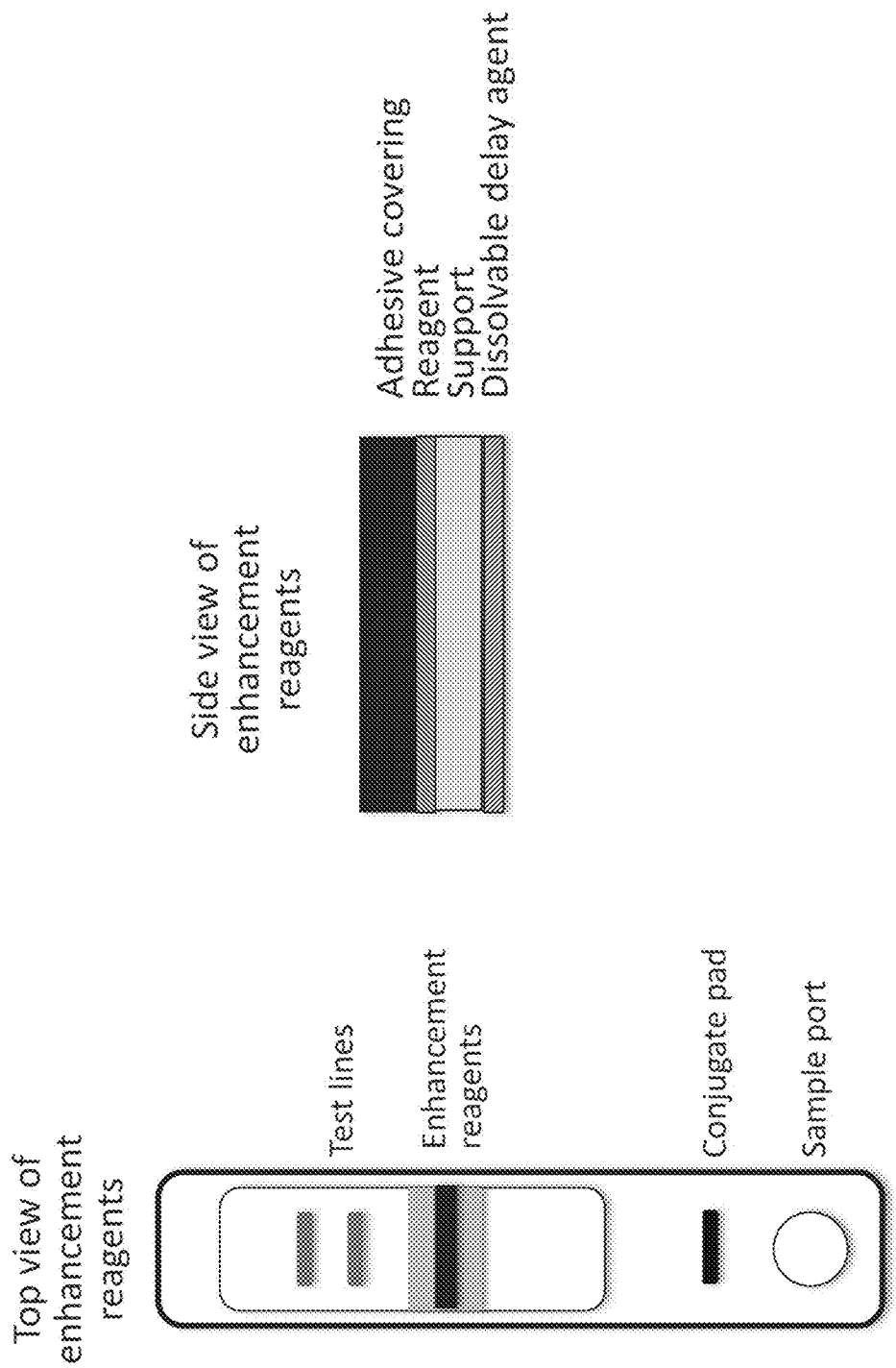
FIG. 8 shows an example of a multi-layer delay pad using a dissolvable layer to control the delay timing.

An additional example of more preferred technology for separating at least one of the reagents from the flowing liquid is shown in FIG. 8. The chemistry delay pad is a multilevel device made as in Example 1 using dye solutions as visual indicators of the delay and water movement. The time delay as shown in Table 1, depends on the amount of dissolvable reagent applied to the surface of the delay pad. This embodiment allows uniform fluid flow and simple manufacturing.

Example

A 10% sucrose solution in water was sprayed in several passes onto a strip of Fischerbrand Q8 ashless filter paper using a Biodot XYZ3060 AirJet sprayer at 1 µL/cm. The paper was died at 37° C. between each pass. The paper was inverted and a test dye solution of bromophenol blue in water was sprayed at 0.7 µL/cm using the Biodot XYZ3060 Biojet sprayer on the back. The delay pad was then dried at 37° C., trimmed, and adhered to a UniSart CN95 polyester-backed nitrocellulose strip below the test line using a covering of OmniMask 813 stencil material. The test line consisted of another line of bromophenol blue applied at 0.7 µL/cm using the Biodot XYZ3060 Biojet sprayer and then dried. The layup was cut into strips, adhered to DCN plastic backing cards (DCN, Carlsbad, Calif.). The plastic backing was cut into the width of the nitrocellulose strip and an absorptive pad attached using the adhesive of the plastic backing for retention of the pad. The finished test system was placed in water with a small amount of sodium carbonate and a movie taken of the flow. The times to start the appearance of the bromophenol dye from the delay pad and the initial movement of the bromophenol blue test line were estimated from the movie are given in Table 1. After 10 minutes all the chemistry had moved in from all the delay pads.

TABLE 1

Timing observed for the delay pads

| Number of passes of sucrose | Time for initial movement of test line (secs) | Time for initial appearance of delay pad reagent (secs) |
|---|---|---|
| 1 | 68 | 142 |
| 2 | 64 | 247 |
| 3 | 60 | 309 |

In all of the above examples, the enhancement reagents may be all the required reagents or just one of them necessary to form the dye. The single reagent would be considered the limiting reagent for the purposes of this disclosure. In all examples, the enhancement reagents (or the limiting reagents) may be applied directly to the strip during manufacture or in pads placed in contact. In all cases, the reagent pads may be any compatible material (such as cellulose) and need not be the more expensive nitrocellulose used for the flow strip.

Dye Chemistry

For the present invention, several types of dye systems could be used that react with palladium nanoparticles and produce a signal detectable either visually or using instrumentation. The dye system should work rapidly at room temperature and form a precipitate that is visually detectable. It should be catalytic under physiological conditions, and work in an aqueous medium. One possible reagent batch comprises chloronapthol (4-CN), N,N'-diethyl-p-phenylenediamine (DEPDA), and hydrogen peroxide. Hydrogen peroxide may be provided in a number of forms including a solution that is added by the user after running the assay for development of the colorimetric signal. However, a dry form of hydrogen peroxide is preferred such as sodium percarbonate, sodium perborate, and urea peroxide, with sodium percarbonate being preferred.

Colorimetric Reagents

Figure 4:
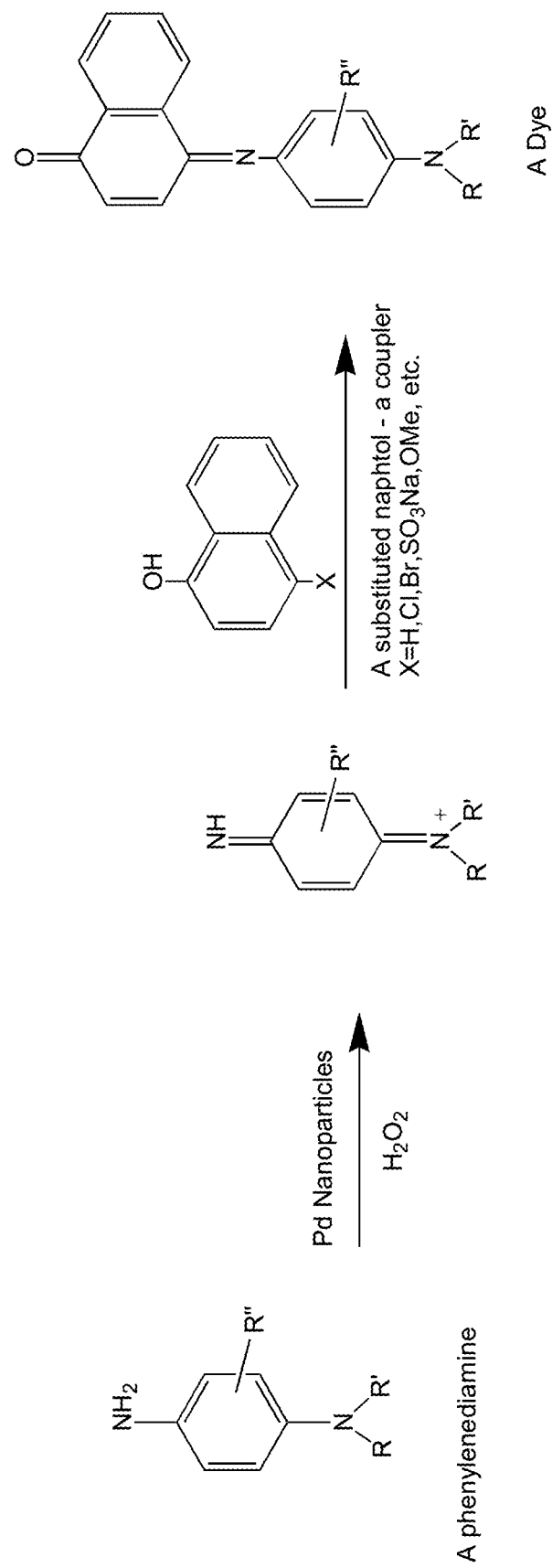
FIG. 4 shows the generalized colorimetric reaction used to detect palladium nanoparticles.

The general colorimetric reaction that is employed to detect palladium nanoparticles is shown in FIG. 4. This chemistry is derived from color photography and the variety of coupling agents and couplers to form various dyes is very large. Most of the chemistry in color photography was focused on having colors of the correct shade and permanence. That is not a requirement for LFIAs since the shade is really an aesthetic requirement in color photography (i.e. you want the correct skin tone to reflect reality) rather than a functional requirement (i.e. see a color form). Additionally, a LFIA is read immediately and rarely requires that the signal be present indifferently, although that may be a helpful attribute in certain circumstances. Thus, the coupling agents and couplers available for LFIAs are quite large.

For use in the catalytic system of the present invention, a substituted para-phenylenediamine is oxidized in the presence of a palladium nanoparticle to form a reactive imine. This will couple with a phenol or napthol derivative to form a colored dye. Generally, napthols give blue or darker colors and phenols provide red to brown colors. Other active methylene compounds are known in the art of color photography and they generally produce yellow dyes. For the purpose of visual detection by the human eye, red, blue, and green dyes are preferred, with blue being most preferred. A more specific colorimetric reaction involves phenylenediamine oxidation and reaction with a napthol, which produces a dark blue dye.

Some examples of a substituted para-phenylenediamine that can be used include N-ethyl-N-(2-hydroxyethyl)-2-methyl-1,4-phenylenediamine (HEPDA) and N,(2-((4-amino-3-methylphenyl)(ethyl)amino)ethylmethanesulfonamide (MSPDA). MSPDA is conventionally used as the color developer in commercial Kodak E-6 color developer so its history as a consumer product is well studied. Some examples of a color coupler include 4-chloro-1-napthol (4-CN), 4-hydroxy-1-napthalenesulfonic acid (4-NSA), and 4-methoxy-1-napthol (4-MN). Note that all the napthols couple in the 4 position to produce the same indiamine dye. 1-napthol produces blue, and 2-napthol produces a green-blue to brown color.

Multiple different dye systems can be used simultaneously. For example, a results window could show a red line, a blue line, and a green line. Many combinations of different color lines are possible.

Other examples of dyes useful with catalytic particles for increased sensitivity in lateral flow immunoassays may be found in substrates for horseradish peroxidase. (Conyers et al., "Chromogenic Substrates for Horseradish Peroxidase," Anal. Biochem., 192, 207-211 (1991) and Marthinus et al., "Substrates for peroxidase assaying," WO 1990006372 (Dec. 1, 1988)). Some of this chemistry was recently incorporated in the use of a LFIA using catalytic palladium. (Tominaga, "Enhanced sensitivity of lateral-flow test strip immunoassays using colloidal palladium nanoparticles and horseradish peroxidase," LWT—Food Science and Technology, 86, 566e570 (2017) and Tominaga, "Rapid detection of *Klebsiella pneumoniae, Klebsiella oxytoca, Raoultella ornithinolytica* and other related bacteria in food by lateral-flow test strip Immunoassays," Journal of Microbiological Methods, 147, 43-49 (2018)). These papers used 3,3-diaminobenzidine (DAB) as the substrate to precipitate a water insoluble dye for the LFIA. In contrast, the paper tried 3,3,5,5-tetramethylbenzidine (TMB) another common substrate for horseradish peroxidase but it formed a water soluble dye that would not precipitate and was thus unsuitable. In addition, the palladium particles used in this paper were very large and not very catalytic and thus the sensitivity increase over conventional gold labels was only 5-10 times in model LFIAs for *Listeria monocytogenes, Escherichia coli* O157:H7, and *Yersinia enterocolitica*. We speculate that the formed dye from DAB was not stable to the oxidation conditions and that over time an equilibrium was form of production and destruction of the dye. This hindered the colorimetric density achieved.

Immobilization of Dye Chemistry

For use in a LFIA the dye formed should not diffuse from the formation site as that keeps a sharp line and a higher sensitivity. The chemistry should produce a dye that precipitates at the reaction site. Some known dyes such as TMB will form water-soluble dyes that are not useful for LFIA. One approach to solve this problem is the use of couplers that release a water solubilizing functionality upon coupling to the color developer. The sulfate group, which provides water solubility, is substituted by the imine. The resulting dye is water insoluble.

Figure 5:
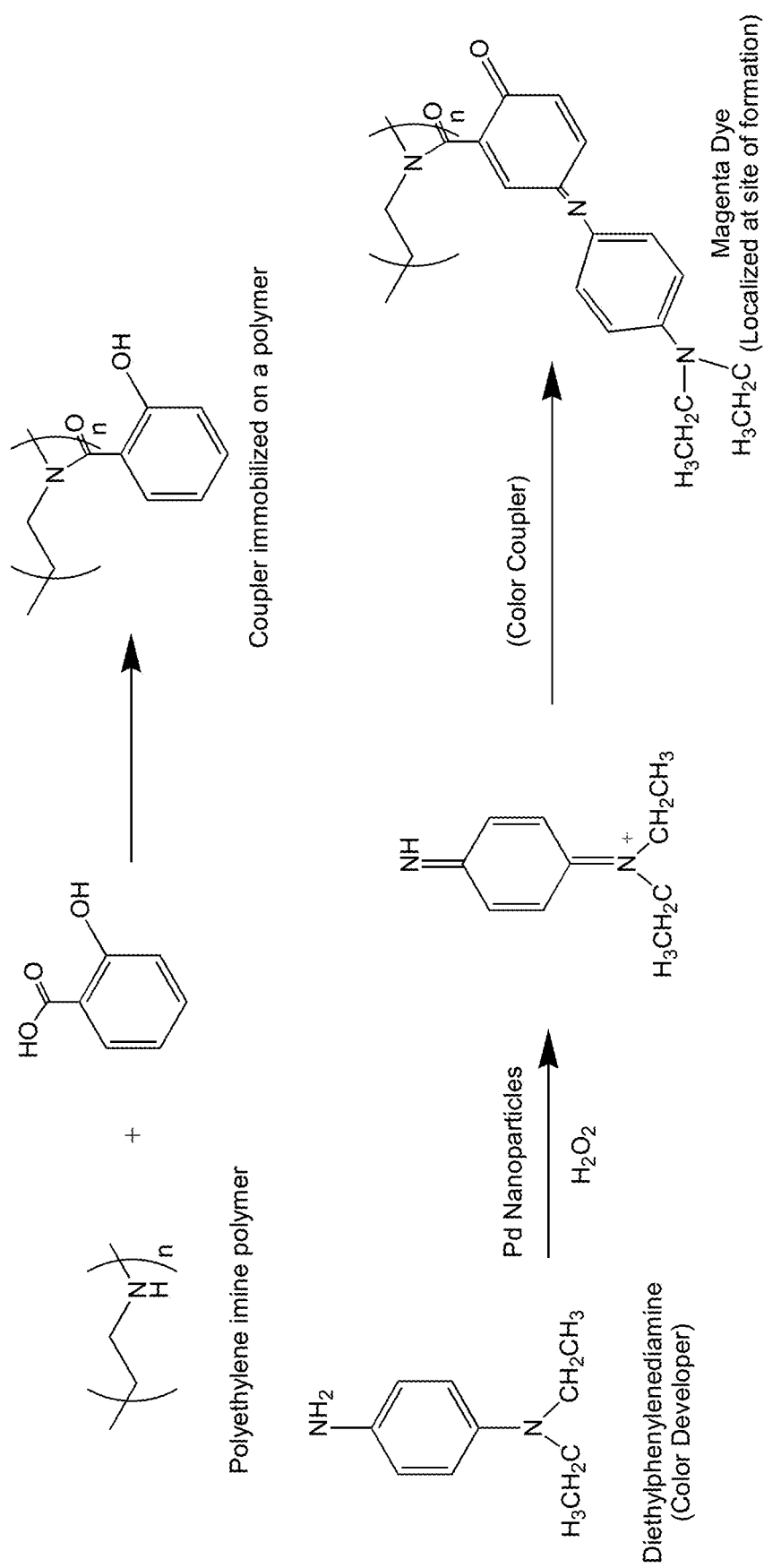
FIG. 5 shows immobilization of a color coupler on a polymer. The immobilization may be employed on a polymer, a biomolecule, a large bead, or the surface of the LFIA strip. For manufacturability, immobilization on beads or a polymer is preferred. Free salicylic acid forms a magenta dye with diethylphenylenediamine that has been oxidized in the presence of the palladium catalyst. This dye is typically water soluble but should be immobilized if the salicylic acid is also immobilized.

To remedy this problem and expand the number of reagents possible and the colors formed, the coupler may be immobilized on a polymer or biomolecule as shown in FIG. 5, with the polymer being a preferred immobilization system due to cost and availability of a wider density of functionalities. Alternatively, the color coupler may be immobilized on a particle as shown in FIG. 6. Additionally, as the color coupler is only present at the site of reaction, the background on the rest of the strip is greatly reduced.

Other Detection Systems

Visual detection of the binding event in a LFIA has the advantage of simplicity but the disadvantage that the human eye is not vary quantitative. Simple camera equipment has been proposed to help read LFIAs and some convenient examples have made it to the commercial marketplace.

Figure 7:
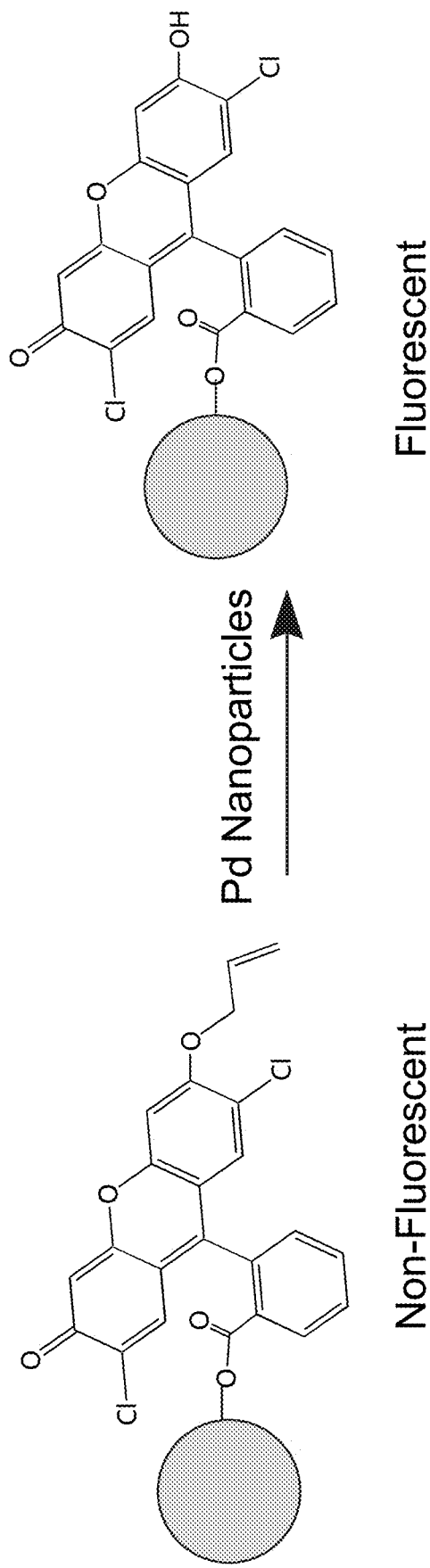
FIG. 7 shows an example of an immobilized fluorescent dye and its development. In this case, the dye is attached to a particle. No hydrogen peroxide is necessary in this system as the Pd just removes the allyl group, which then allows the dichlorofluorescein to fluoresce. The fluorescence would be measured instrumentally.

If hardware is being used to read the LFIA, increased sensitivity can be achieved by using chemiluminescence or fluorescence. These systems increase sensitivity by reducing the background and allow the detection of photons—a process that can be very sensitive electronically. The palladium nanoparticles can catalyze the formation of fluorescent dyes or oxidize light emitting substrates such as luminol and thus increase sensitivity in two ways—catalytically and through the electronic detection of photons. Because most fluorescent dyes are water soluble, they would need to be immobilized on a particle or on a surface, as shown in FIG. 7 to be immobilized on a particle, to be useful in the present invention as they need to stay at the site of biologically binding to stay concentrated.

An immobilized chemiluminescent dye can be attached to a particle or a surface. Hydrogen peroxide is catalytically reacted with the luminol derivative, which then emits light. The light can be measured visually, photographically, or instrumentally. An example of use of chemiluminescent beads may be found in Knox van Dyke, et al., "Luminol- or Lucigenin-Coated Micropolystyrene Beads, a Single Reagent to Study Opsonin-Independent Phagocytosis by Cellular Chemiluminescence: Reaction with Human Neutrophils, Monocytes, and Differentiated HL60 Cells," Microchemical Journal, 41, 196-209 (1990), the entire contents of which is incorporated by reference.

Palladium Nanoparticles

Palladium nanoparticles provide increased sensitivity in lateral flow immunoassays. In preparing the colloidal palladium, an aldehyde coating is developed that does not seriously affect the catalytic activity but allows rapid attachment of biomolecules. The preparation conditions allow production of colloidal palladium of a very small and uniform size that does not precipitate from solution on storage and is mobile in a LFIA.

In lateral flow immunoassays, particle labels have multiple roles in overall test performance. It is known in the art that the optimal size for gold is 20-60 nm. This is based on absorption characteristics (color) for visual reading and not necessarily on flow characteristics. Palladium particles less than 20 nm can be used in immunoassays. For assays, the particle size needs to be such that the particle flows along the LFIA strip and stays in solution. The particle should not fall out of solution within the assay. Heating the particles too much during synthesis and using the wrong ratio of starting materials can lead to particle sizes that are too big for good LFIA performance.

The nanoparticles used in the present invention are small. These nanoparticles will not spin-down in a centrifuge at 15 K-g not at 38,500×g. They are not readily separated by gel electrophoresis. They are not readily separated on a sizing gel. They are not readily determined by dynamic light scattering (DLS). The brown color of the resultant colloidal solution attests to the small size of the palladium particles. Particles that are larger due to inadequate preparation or coagulation do not work as well in the catalytic systems described in the instant patent.

The reducing agent can affect the particle size. If the pH is too high, the reduction will be too rapid, and the particles will be too large. For example, using formaldehyde in a basic solution will lead to a quick reduction and particles that are too big. In the present invention, glutaraldehyde provides for a slow reduction. It also appears to coat the particles with a coating, which binds the protein and puts a negative charge on the particles from the oxidation of the glutaraldehyde to a carboxylic acid.

The above descriptions are those of the preferred embodiments of the invention. Various modifications and variations are possible in light of the above teachings without departing from the spirit and broader aspects of the invention. It is therefore to be understood that the claimed invention may be practiced otherwise than as specifically described. Any references to claim elements in the singular, for example, using the articles "a," "an," "the," or "said," is not to be construed as limiting the element to the singular.

What is claimed is:

1. A method for improving a catalytic signal for a lateral flow immunoassay, comprising:
   providing a lateral flow immunoassay comprising
      a source of hydrogen peroxide, wherein the source of hydrogen peroxide comprises sodium percarbonate;
      a substituted para-phenylenediamine;
      a phenol or napthol;
      palladium nanoparticles; and
      a time delay mechanism; and
   interacting the substituted para-phenylenediamine, the phenol or napthol, and the hydrogen peroxide with the palladium nanoparticles to form a dye that is a visual label for the lateral flow immunoassay, wherein the time delay mechanism delays the interaction of at least one of the substituted para-phenylenediamine, the phenol or napthol, or the hydrogen peroxide with the palladium nanoparticles thereby improving the catalytic signal.

2. A method for improving a catalytic signal for a lateral flow immunoassay, comprising:

providing a lateral flow immunoassay comprising
  a source of hydrogen peroxide;
  a substituted para-phenylenediamine, wherein the substituted para-phenylenediamine comprises N-ethyl-N-(2-hydroxyethyl)-2-methyl-1,4-phenylenediamine (HEPDA) or N,(2-((4-amino-3-methylphenyl)(ethyl)amino)ethylmethanesulfonamide (MSPDA);
  a phenol or napthol;
  palladium nanoparticles; and
  a time delay mechanism; and
interacting the substituted para-phenylenediamine, the phenol or napthol, and the hydrogen peroxide with the palladium nanoparticles to form a dye that is a visual label for the lateral flow immunoassay, wherein the time delay mechanism delays the interaction of at least one of the substituted para-phenylenediamine, the phenol or napthol, or the hydrogen peroxide with the palladium nanoparticles thereby improving the catalytic signal.

3. A method for improving a catalytic signal for a lateral flow immunoassay, comprising:
  providing a lateral flow immunoassay comprising
    a source of hydrogen peroxide;
    a substituted para-phenylenediamine;
    a phenol or napthol;
    palladium nanoparticles; and
    a time delay mechanism, wherein the time delay mechanism comprises using a dissolving material to slow a fluid flow in the lateral flow immunoassay; and
  interacting the substituted para-phenylenediamine, the phenol or napthol, and the hydrogen peroxide with the palladium nanoparticles to form a dye that is a visual label for the lateral flow immunoassay, wherein the time delay mechanism delays the interaction of at least one of the substituted para-phenylenediamine, the phenol or napthol, or the hydrogen peroxide with the palladium nanoparticles thereby improving the catalytic signal.

4. A method for improving a catalytic signal for a lateral flow immunoassay, comprising:
  providing a lateral flow immunoassay comprising
    a source of hydrogen peroxide;
    a substituted para-phenylenediamine;
    a phenol or napthol;
    palladium nanoparticles; and
    a time delay mechanism, wherein the time delay mechanism comprises using a serpentine flow in the lateral flow immunoassay; and
  interacting the substituted para-phenylenediamine, the phenol or napthol, and the hydrogen peroxide with the palladium nanoparticles to form a dye that is a visual label for the lateral flow immunoassay, wherein the time delay mechanism delays the interaction of at least one of the substituted para-phenylenediamine, the phenol or napthol, or the hydrogen peroxide with the palladium nanoparticles thereby improving the catalytic signal.

5. A method for improving a catalytic signal for a lateral flow immunoassay, comprising:
  providing a lateral flow immunoassay comprising
    a source of hydrogen peroxide;
    a substituted para-phenylenediamine;
    a phenol or napthol;
    palladium nanoparticles; and
    a time delay mechanism, wherein the time delay mechanism comprises combining a reducing agent with the substituted para-phenylenediamine, the phenol or napthol, or the hydrogen peroxide before interaction with the palladium nanoparticles; and
  interacting the substituted para-phenylenediamine, the phenol or napthol, and the hydrogen peroxide with the palladium nanoparticles to form a dye that is a visual label for the lateral flow immunoassay, wherein the time delay mechanism delays the interaction of at least one of the substituted para-phenylenediamine, the phenol or napthol, or the hydrogen peroxide with the palladium nanoparticles thereby improving the catalytic signal.

* * * * *